a

US009907748B2

(12) United States Patent
Borschke et al.

(10) Patent No.: US 9,907,748 B2
(45) Date of Patent: Mar. 6, 2018

(54) EXCIPIENTS FOR NICOTINE-CONTAINING THERAPEUTIC COMPOSITIONS

(75) Inventors: August Joseph Borschke, Winston-Salem, NC (US); Darrell Holton, Jr., Clemmons, NC (US)

(73) Assignee: Niconovum USA, Inc., Winston-Salem, NC (US)

( * ) Notice: Subject to any disclaimer, the term of this patent is extended or adjusted under 35 U.S.C. 154(b) by 1091 days.

(21) Appl. No.: 13/278,877

(22) Filed: Oct. 21, 2011

(65) Prior Publication Data

US 2013/0098377 A1    Apr. 25, 2013

(51) Int. Cl.
*A61K 31/465*   (2006.01)
*A61K 9/00*   (2006.01)
*A61K 9/68*   (2006.01)

(52) U.S. Cl.
CPC .......... *A61K 9/0056* (2013.01); *A61K 9/0058* (2013.01); *A61K 31/465* (2013.01); *A61K 9/0043* (2013.01)

(58) Field of Classification Search
CPC .. A61K 31/465; A61K 9/0058; A61K 9/0056; A61K 9/0043
See application file for complete search history.

(56) References Cited

U.S. PATENT DOCUMENTS

| | | |
|---|---|---|
| 3,845,217 A | 10/1974 | Ferno et al. |
| 3,877,468 A | 4/1975 | Lichtneckert et al. |
| 3,901,248 A | 8/1975 | Lichtneckert et al. |
| 4,284,809 A | 8/1981 | Sih |
| 4,579,858 A | 4/1986 | Fernö et al. |
| 4,655,231 A | 4/1987 | Ray et al. |
| 4,800,903 A | 1/1989 | Ray et al. |
| 4,907,605 A | 3/1990 | Ray et al. |
| 4,967,773 A | 11/1990 | Shaw |
| 5,110,605 A | 5/1992 | Acharya |
| 5,147,654 A | 9/1992 | Place et al. |
| 5,154,927 A | 10/1992 | Song et al. |
| 5,167,242 A | 12/1992 | Turner et al. |
| 5,362,496 A | 11/1994 | Baker et al. |
| 5,512,306 A | 4/1996 | Carlsson et al. |
| 5,525,351 A | 6/1996 | Dam |
| 5,543,424 A | 8/1996 | Carlsson et al. |
| 5,549,906 A | 8/1996 | Santus |
| 5,656,255 A | 8/1997 | Jones |
| 5,662,920 A | 9/1997 | Santus |
| 5,711,961 A | 1/1998 | Reiner et al. |
| 5,733,574 A | 3/1998 | Dam |
| 5,811,126 A | 9/1998 | Krishnamurthy |
| 5,939,100 A | 8/1999 | Albrechtsen et al. |
| 6,024,097 A | 2/2000 | Von Wielligh |
| 6,024,981 A | 2/2000 | Khankari et al. |
| 6,083,531 A | 7/2000 | Humbert-Droz et al. |
| 6,090,401 A | 7/2000 | Gowan, Jr. et al. |
| 6,098,632 A | 8/2000 | Turner et al. |
| 6,110,495 A | 8/2000 | Dam |
| 6,234,169 B1 | 5/2001 | Bulbrook et al. |
| 6,248,760 B1 | 6/2001 | Wilhelmsen |
| 6,268,386 B1 | 7/2001 | Thompson |
| 6,280,761 B1 | 8/2001 | Santus |
| 6,319,510 B1 | 11/2001 | Yates |
| 6,322,806 B1 | 11/2001 | Ream et al. |
| 6,344,222 B1 | 2/2002 | Cherukuri et al. |
| 6,355,265 B1 | 3/2002 | Ream et al. |
| 6,358,060 B2 | 3/2002 | Pinney et al. |
| 6,426,090 B1 | 7/2002 | Ream et al. |
| 6,488,953 B2 | 12/2002 | Halliday et al. |
| 6,569,463 B2 | 5/2003 | Patel et al. |
| 6,583,160 B2 | 6/2003 | Smith et al. |
| 6,585,997 B2 | 7/2003 | Moro et al. |
| 6,596,740 B2 | 7/2003 | Jones |
| 6,676,959 B1 | 1/2004 | Andersson et al. |
| 6,709,671 B2 | 3/2004 | Zerbe et al. |
| 6,773,716 B2 | 8/2004 | Ream et al. |
| 6,874,507 B2 | 4/2005 | Farr |
| 6,893,654 B2 | 5/2005 | Pinney et al. |
| 7,025,983 B2 | 4/2006 | Leung et al. |
| 7,101,579 B2 | 9/2006 | Athanikar et al. |
| 7,105,173 B1 | 9/2006 | Rolling |
| 7,115,297 B2 | 10/2006 | Stillman |

(Continued)

FOREIGN PATENT DOCUMENTS

| | | |
|---|---|---|
| EP | 1618803 | 1/2006 |
| EP | 2 233 134 | 9/2010 |
| JP | H05-255066 | 10/1993 |
| JP | 2003-504165 | 2/2003 |

(Continued)

OTHER PUBLICATIONS

PCT International Preliminary Report on Patentability for PCT/US2012/061023 (dated Jan. 16, 2014).*

*Primary Examiner* — Michael H Wilson
*Assistant Examiner* — Dionne Walls Mayes
(74) *Attorney, Agent, or Firm* — Womble Bond Dickinson (US) LLP

(57) ABSTRACT

A composition intended to be employed for therapeutic purposes incorporates an active ingredient (e.g., a source of nicotine) and at a non-active ingredient that is carried by a porous substrate. The non-active ingredient can be a substance that has the capability of affecting the pH of the biological system to which it is applied (e.g., basic substance and/or buffering agent is sorbed onto the porous carrier, so as to be in intimate contact with that carrier). Representative forms of nicotine include free base (e.g., as a mixture of nicotine and microcrystalline cellulose), a nicotine salt (e.g., as nicotine bitartrate) and nicotine polacrilex. The basic substance can be sodium carbonate, and the porous substrate can be microcrystalline cellulose. The composition is useful for treatment of central nervous system conditions, diseases, and disorders, and can be used as a nicotine replacement therapy.

18 Claims, No Drawings

(56) References Cited

U.S. PATENT DOCUMENTS

| | | |
|---|---|---|
| 7,163,705 B2 | 1/2007 | Johnson et al. |
| 7,208,186 B2 | 4/2007 | Hirota |
| 7,374,779 B2 | 5/2008 | Chen et al. |
| 7,435,749 B2 | 10/2008 | Knight |
| 7,491,406 B2 | 2/2009 | Leung et al. |
| 2001/0016593 A1 | 8/2001 | Wilhelmsen |
| 2003/0159702 A1 | 8/2003 | Lindell et al. |
| 2003/0176467 A1 | 9/2003 | Andersson et al. |
| 2003/0235617 A1 | 12/2003 | Martino et al. |
| 2004/0034068 A1 | 2/2004 | Warchol et al. |
| 2004/0096501 A1 | 5/2004 | Vaya et al. |
| 2004/0101543 A1 | 5/2004 | Liu et al. |
| 2004/0191322 A1* | 9/2004 | Hansson ............ 424/489 |
| 2004/0194793 A1 | 10/2004 | Lindell et al. |
| 2005/0053665 A1 | 3/2005 | Ek et al. |
| 2006/0018840 A1 | 1/2006 | Lechuga-Ballesteros et al. |
| 2006/0099300 A1 | 5/2006 | Andersen et al. |
| 2006/0120974 A1 | 6/2006 | McNeight |
| 2006/0121156 A1 | 6/2006 | Andersen et al. |
| 2006/0165842 A1 | 7/2006 | Andersen et al. |
| 2006/0171994 A1 | 8/2006 | Dupinay et al. |
| 2006/0198873 A1 | 9/2006 | Chan et al. |
| 2006/0204451 A1 | 9/2006 | Salini |
| 2006/0204559 A1 | 9/2006 | Bess et al. |
| 2006/0240087 A1 | 10/2006 | Houze et al. |
| 2006/0246174 A1 | 11/2006 | Andersen et al. |
| 2006/0275344 A1 | 12/2006 | Mody et al. |
| 2007/0014887 A1 | 1/2007 | Cherukuri et al. |
| 2007/0081949 A1 | 4/2007 | Dam et al. |
| 2007/0163610 A1 | 7/2007 | Lindell et al. |
| 2007/0269386 A1 | 11/2007 | Steen et al. |
| 2007/0269492 A1 | 11/2007 | Steen et al. |
| 2008/0020050 A1 | 1/2008 | Chau et al. |
| 2008/0286340 A1 | 11/2008 | Andersen et al. |
| 2008/0292683 A1 | 11/2008 | Sanghvi et al. |
| 2008/0302375 A1 | 12/2008 | Andersen et al. |
| 2009/0004248 A1 | 1/2009 | Bunick et al. |
| 2009/0005423 A1 | 1/2009 | Gonda |
| 2009/0023819 A1 | 1/2009 | Axelsson |
| 2009/0081291 A1 | 3/2009 | Gin et al. |
| 2009/0092573 A1 | 4/2009 | Andersen |
| 2009/0293895 A1 | 12/2009 | Axelsson et al. |
| 2010/0004294 A1 | 1/2010 | Axelsson et al. |
| 2010/0018539 A1 | 1/2010 | Brinkley et al. |
| 2010/0061940 A1 | 3/2010 | Axelsson et al. |
| 2010/0247586 A1* | 9/2010 | Hugerth et al. ............ 424/401 |
| 2010/0256197 A1 | 10/2010 | Lockwood, Jr. et al. |
| 2010/0260690 A1* | 10/2010 | Kristensen et al. ............ 424/48 |
| 2011/0070286 A1* | 3/2011 | Hugerth et al. ............ 424/440 |
| 2011/0268809 A1 | 11/2011 | Brinkley et al. |
| 2011/0274628 A1 | 11/2011 | Borschke |

FOREIGN PATENT DOCUMENTS

| | | |
|---|---|---|
| JP | 2005-533770 | 11/2005 |
| JP | 2011-506384 | 3/2011 |
| KR | 2010 0117950 | 11/2010 |
| WO | WO 91/09599 | 7/1991 |
| WO | WO 03/055486 | 7/2003 |
| WO | WO 2004/056363 | 7/2004 |
| WO | WO 2005/023226 | 3/2005 |
| WO | WO 2007/104573 | 9/2007 |
| WO | WO 2007/104574 | 9/2007 |
| WO | WO 2008/037470 | 4/2008 |
| WO | WO 2008/069921 | 6/2008 |
| WO | WO 2009/037319 | 3/2009 |
| WO | WO 2010/044736 | 4/2010 |

* cited by examiner

EXCIPIENTS FOR NICOTINE-CONTAINING THERAPEUTIC COMPOSITIONS

FIELD OF THE INVENTION

The present invention relates to compositions that contain active ingredients that can be characterized as those having a pharmacological effect and that can be considered to be useful for therapeutic purposes, and in particular, to such compositions that also contain excipients.

BACKGROUND OF THE INVENTION

Central nervous system (CNS) conditions, diseases, or disorders can be drug induced; can be attributed to genetic predisposition, infection or trauma; or can be of unknown etiology. They comprise neuropsychiatric disorders, neurological diseases and mental illnesses; and include neurodegenerative diseases, behavioral disorders, cognitive disorders and cognitive affective disorders. The clinical manifestations of several CNS conditions, diseases or disorders have been attributed to CNS dysfunction (i.e., disorders resulting from inappropriate levels of neurotransmitter release, inappropriate properties of neurotransmitter receptors, and/or inappropriate interaction between neurotransmitters and neurotransmitter receptors).

Nicotinic compounds, such as nicotine, are capable of affecting nicotinic acetylcholinergic receptors (nAChRs). Subtypes of nAChRs exist in both the CNS and the peripheral nervous system (PNS), but the distribution of subtypes is heterogeneous. For instance, certain subtypes which are predominant in vertebrate brain, others predominate at the autonomic ganglia, and others predominate at neuromuscular junction. Activation of nAChRs by nicotinic compounds results in neurotransmitter release. See, for example, Dwoskin et al., *Exp. Opin. Ther. Patents*, 10: 1561-1581 (2000); Schmitt et al., *Annual Reports in Med. Chem.*, 35: 41-51 (2000); Huang et al., *J. Am. Chem. Soc.*, 127: 14401-14414 (2006); Arneric et al., *Biochem. Pharmacol.*, 74: 1092-1101 (2007) and Millar, *Biochem. Pharmacol.*, 78: 766-776 (2009), which are incorporated herein by reference.

It has been suggested that administration of nicotine, and other nicotinic compounds, can result in various pharmacological effects. See, for example, U.S. Pat. No. 5,583,140 to Bencherif et al.; U.S. Pat. No. 5,723,477 to McDonald et al.; U.S. Pat. No. 7,001,900 to Jacobsen et al.; U.S. Pat. No. 7,135,484 to Dart et al. and U.S. Pat. No. 7,214,686 to Bencherif et al.; US Pat. Pub. No. 2010/0004451 to Ahmad et al. and U.S. patent application Ser. No. 12/775,910 to Borschke, filed May 7, 2010; which are incorporated herein by reference. As a result, it has been suggested that nicotine, and other nicotinic compounds, can exhibit utility as active ingredients in the treatment of a wide variety of conditions, diseases, and disorders, including those that affect the CNS. Additionally, administration of nicotine and nicotinic compounds has been proposed for treatment of certain other conditions, diseases, and disorders. See, for example, U.S. Pat. No. 5,604,231 to Smith et al.; U.S. Pat. No. 5,811,442 to Bencherif et al.; U.S. Pat. No. 6,238,689 to Rhodes et al. and U.S. Pat. No. 6,489,349 to Bencherif et al., which are incorporated herein by reference. Furthermore, administration of nicotine has been employed in an effort to help cigarette smokers quit smoking (i.e., as a smoking cessation aid). For example, nicotine has been an active ingredient of various types of so-called "nicotine replacement therapy" or "NRT" products. See, for example, the background art set forth in U.S. patent application Ser. No. 12/769,335 to Brinkley et al., filed Apr. 28, 2010, which is incorporated herein by reference.

It has been proposed to administer nicotine using a transdermal patch. Representative types of nicotine-containing transdermal patch products have been marketed under the tradenames "Habitrol," "Nicoderm," "Nicorette," "Nicorette CQ," "Nicotinell" and "ProStep." See also, for example, U.S. Pat. No. 4,597,961 to Etscom; U.S. Pat. No. 5,298,257 to Bannon et al.; U.S. Pat. No. 5,603,947 to Wong et al.; U.S. Pat. No. 5,834,011 to Rose et al.; U.S. Pat. No. 6,165,497 to Osborne et al. and U.S. Pat. No. 6,676,959 to Anderson et al., which are incorporated herein by reference. It also has been suggested that transdermal administration of nicotine can be accompanied by ingestion of other types of nicotine-containing products. See, for example, U.S. Pat. No. 5,593,684 to Baker et al.; US Pat. Pub. No. 2009/0004249 to Gonda; and Fagerstrom, *Health Values*, 18:15 (1994), which are incorporated herein by reference.

One particularly popular way to provide for oral administration of nicotine has been through the use of nicotine-containing gum. Nicotine-containing gum products have been marketed under the tradenames "Nicorette," "Nicotinell" and "Zonnic." See also, for example, U.S. Pat. No. 3,845,217 to Ferno et al.; U.S. Pat. No. 3,877,468 to Lichtneckert et al.; U.S. Pat. No. 3,901,248 to Lichtneckert et al.; U.S. Pat. No. 6,344,222 to Cherukuri et al.; U.S. Pat. No. 6,358,060 to Pinney et al.; U.S. Pat. No. 6,773,716 to Ream et al. and U.S. Pat. No. 6,893,654 to Pinney et al.; and US Pat. Pub. No. 2004/0191322 to Hansson, which are incorporated herein by reference.

Another way that has been employed to provide oral administration of nicotine has been through the use of nicotine-containing lozenge or tablet types of products. Nicotine-containing lozenge, mini lozenge, tablet, and microtab types of products have been marketed under the tradenames "Commit," "Nicorette," "Nicotinell" and "NiQuitin." See also, for example, U.S. Pat. No. 5,110,605 to Acharya; U.S. Pat. No. 5,733,574 to Dam; U.S. Pat. No. 6,280,761 to Santus; U.S. Pat. No. 6,676,959 to Andersson et al. and U.S. Pat. No. 6,248,760 to Wilhelmsen; US Pat. Pub. Nos. 2001/0016593 to Wilhelmsen and 2010/0004294 to Axelsson et al., which are incorporated herein by reference.

Nicotine also has been administered in the form of nasal or oral sprays. Various exemplary ways to administer nicotine in the form of a nasal spray are set forth in U.S. Pat. No. 4,579,858 to Ferno et al.; U.S. Pat. No. 5,656,255 to Jones and U.S. Pat. No. 6,596,740 to Jones, which are incorporated herein by reference. Various exemplary ways to administer nicotine in the form of an oral spray, such as for buccal administration, are set forth in U.S. Pat. No. 6,024,097 to Von Wielligh; US Pat. Pub. Nos. 2003/0159702 to Lindell et al.; 2007/0163610 to Lindell et al. and 2009/0023819 to Axelsson; EP 1458388 to Lindell et al.; and PCT WO 2008/037470 to Axelsson et al., which are incorporated herein by reference. Nicotine-containing sprays have been marketed under the tradenames "Nicotrol NS," "Quit" and "Zonnic."

Various other ways to administer nicotine for the purpose of providing a therapeutic effect have been proposed. For example, it has been suggested that nicotine can be incorporated into orally dissolving films (e.g., U.S. Pat. No. 6,709,671 to Zerbe et al.; U.S. Pat. No. 7,025,983 to Leung et al.; and U.S. Pat. No. 7,491,406 to Leung et al.; and US Pat. Pub. Nos. 2006/0198873 to Chan et al.; 2006/0204559 to Bess et al. and 2010/0256197 to Lockwood et al.); oral osmotic devices (e.g., U.S. Pat. No. 5,147,654 to Place et al.); gum pads (e.g., U.S. Pat. No. 6,319,510 to Yates); oral patches (e.g., US Pat. Pub. No. 2006/0240087 to Houze et al.); snuff-type forms in pouches or sachets (e.g., U.S. Pat. No. 4,907,605 to Ray et al. and US Pat. Pub. No. 2009/0293895 to Axelsson et al.); lip balm (e.g., U.S. Pat. No. 7,105,173 to Rolling) and beverages (e.g., U.S. Pat. No. 6,268,386 to Thompson; U.S. Pat. No. 7,115,297 to Stillman and U.S. Pat. No. 7,435,749 to Knight). It also has been suggested that nicotine can be delivered using various types of inhalation devices and vapor delivery systems (e.g., U.S. Pat. No. 4,284,809 to Ray; U.S. Pat. No. 4,800,903 to Ray et al.; U.S. Pat. No. 6,234,169 to Bulbrook et al. and U.S. Pat. No. 6,874,507 to Farr; and US Pat. Pub. Nos. 2006/0018840 to Lechuga-Ballesteros and 2009/0005423 to Gonda; and EP 1618803 to Hon).

It would be desirable to provide a composition capable of delivering or administering active ingredient for therapeutic purposes, particularly by way of nasal or oral administration. For example, it would be desirable to provide a formulation incorporating at least one active ingredient and at least one excipient.

SUMMARY OF THE INVENTION

In one aspect, the present invention relates to a composition incorporating at least one active ingredient and at least one excipient. Representative active ingredients are those that can be characterized as having a pharmacological effect, and that can be used for therapeutic purposes. Representative active ingredients can be nicotinic compounds (e.g., nicotine-containing compositions) intended to be employed for therapeutic purposes (e.g., nicotinic antagonists or nicotinic agonists). The composition has a pharmaceutically acceptable form (e.g., as a drug or as a dietary supplement), and most preferably is adapted for nasal or oral delivery. The composition incorporates at least one source of active ingredient, and in addition, at least one non-active ingredient.

In another aspect, the present invention relates to a composition that is composed of an intimate admixture of at least one non-active ingredient and a porous carrier (e.g., a carrier that has a solid form, and preferably a particulate form). In one highly preferred embodiment, the non-active ingredient is a material that possesses the ability to alter the pH of the biological system to which it is administered. For example, acidic material and/or buffering agent, or basic material and/or a buffering agent, can be sorbed onto or otherwise provided in intimate contact with a porous particulate carrier (e.g., microcrystalline cellulose). As a result, a composition adapted for oral administration of nicotinic compound (e.g., for buccal absorption of nicotinic compound) can be enhanced by utilizing an excipient that is composed of basic material and/or buffering agent in combination with microcrystalline cellulose, wherein the nicotinic compound is employed in an amount sufficient to provide a desired therapeutic effect, and the excipient that is composed of basic material and/or buffering agent in intimate contact with the microcrystalline cellulose is employed in an amount sufficient to enhance the uptake of nicotinic compound within the biological system to which the composition is administered.

By placing the porous carrier in intimate contact with the non-active ingredient, the non-active ingredient can be physically separated or segregated from the nicotine in the resulting therapeutic composition. Providing the non-active ingredient, such as a base or buffering agent, in intimate contact with the porous carrier can provide several benefits, including: (1) reducing or eliminating the ability of the non-active ingredient to react or otherwise interact in a disadvantageous manner with the nicotine component during storage of the therapeutic compositions of the invention; (2) improving ease of handling of the non-active ingredient (e.g., by placing such an ingredient in the form of a flowable, particulate material); and (3) enhancing control and measurability of the amount of non-active ingredient used in a therapeutic composition of the invention. These benefits can be accomplished in certain embodiments of the invention while still enabling the non-active ingredient to be released or dispersed from the therapeutic composition of the invention in a timely fashion.

Compositions of the present invention, including compositions incorporating other pharmaceutically acceptable excipient ingredients, can be provided in forms suitable for administration to human subjects, particularly in forms adapted for oral ingestion, and most preferably in forms adapted for buccal administration of active ingredient. Exemplary formats and configurations for oral administration of nicotine-containing compositions for therapeutic purposes include gum, tablet, lozenge, mini lozenge, microtab, film and pouch types of products.

Typically, a composition incorporating microcrystalline cellulose in an intimate relationship with the basic material and/or buffering agent is incorporated into a formulation also incorporating at least one form of nicotinic compound. For example, the nicotinic compound can be nicotine, and the form of nicotine can be as a free base (e.g., as a mixture of nicotine free base and a porous particulate carrier such as microcrystalline cellulose), a nicotine salt (e.g., as nicotine tartrate or nicotine bitartrate or another organic acid salt of nicotine), as a resin complex of nicotine (e.g., nicotine polacrilex), or as a solvate or other suitable form.

In one particular embodiment, the invention provides a nicotine-containing pharmaceutical composition comprising a source of nicotine and a mixture of a porous carrier and a non-active ingredient sorbed onto the porous carrier, the non-active ingredient being in the form of a base or a buffering agent, wherein the composition is in a pharmaceutically acceptable form adapted for oral or nasal delivery of the composition. The non-active ingredient is typically a base or a buffering agent that buffers in a basic pH range or a combination thereof, with exemplary non-active ingredients including sodium carbonate, sodium bicarbonate, trisodium phosphate, and combinations thereof. The mixture can comprise at least about 70 weight percent of the porous carrier (such as microcrystalline cellulose) and up to about 30 weight percent of the non-active ingredient, based on the total weight of the mixture. The mixture of porous carrier and non-active ingredient can further include an outer protective coating, such as various enteric coating materials known in the art (e.g., acrylic polymers such as those available under the tradename EUDRAGIT®). As noted above, the source of nicotine can have a free base form, and the nicotine free base also can be sorbed onto a second porous carrier, such as microcrystalline cellulose.

In another aspect, the present invention relates to a method for treating a condition, disease or disorder responsive to an active ingredient. For example, a condition, disease or disorder responsive to treatment by stimulation of nicotinic acetylcholinergic receptors can be treated by orally or nasally administering an effective amount of a formulation incorporating at least one nicotinic compound and at least one excipient composed of basic substance and/or buffering agent incorporated with or carried by a porous particulate carrier (e.g., nicotine in intimate combination with a composition composed of microcrystalline cellulose and basic material and/or buffering agent) to a human subject in need of treatment.

Exemplary conditions that can be treated using the compositions of the present invention are dependent upon the active ingredient that is employed. For example, active ingredients that are characterized as nicotinic compounds can be used to treat a wide variety of diseases and disorders, including various diseases and disorders affecting the central nervous system. Additionally, the compositions incorporating nicotinic compounds (e.g., nicotine) can be used as a smoking cessation aids.

DETAILED DESCRIPTION OF THE PREFERRED EMBODIMENTS

The present inventions now will be described more fully hereinafter. The invention may be embodied in many different forms and should not be construed as limited to the embodiments set forth herein; rather, these embodiments are provided so that this disclosure will satisfy applicable legal requirements. As used in this specification and the claims, the singular forms "a," "an," and "the" include plural referents unless the context clearly dictates otherwise.

The present invention involves providing a composition that can be used for therapeutic purposes. That is, the composition can be used to treat the cause or symptoms associated with a disease or ailment, or otherwise provide for the well being of the subject to which the composition is administered. The composition can be used as a pharmaceutical composition or as a dietary supplement. The composition incorporates at least one active ingredient, and the composition can be suitably adapted for nasal or oral delivery of that active ingredient.

One particularly preferred active ingredient is a compound that can be characterized as a nicotinic compound. Various nicotinic compounds, and methods for their administration, are set forth in U.S. patent application Ser. No. 12/775,910, filed May 7, 2010, to Borschke, which is incorporated herein by reference. As used herein, "nicotinic compound" or "source of nicotine" often refers to naturally-occurring or synthetic nicotinic compound unbound from a plant material, meaning the compound is at least partially purified and not contained within a plant structure, such as a tobacco leaf. Most preferably, nicotine is naturally-occurring and obtained as an extract from a *Nicotiana* species (e.g., tobacco). The nicotine can have the enantiomeric form S(−)-nicotine, R(+)-nicotine, or a mixture of S(−)-nicotine and R(+)-nicotine. Most preferably, the nicotine is in the form of S(−)-nicotine (e.g., in a form that is virtually all S(−)-nicotine) or a racemic mixture composed primarily or predominantly of S(−)-nicotine (e.g., a mixture composed of about 95 weight parts S(−)-nicotine and about 5 weight parts R(+)-nicotine). Most preferably, the nicotine is employed in virtually pure form or in an essentially pure form. Highly preferred nicotine that is employed has a purity of greater than about 95 percent, more preferably greater than about 98 percent, and most preferably greater than about 99 percent, on a weight basis. Despite the fact that nicotine can be extracted from *Nicotiana* species, it is highly preferred that the nicotine (and the composition and products produced in accordance with the present invention) are virtually or essentially absent of other components obtained from or derived from tobacco.

Nicotinic compounds can include nicotine in free base form, salt form, as a complex, or as a solvate. See, for example, the discussion of nicotine in free base form in US Pat. Pub. No. 2004/0191322 to Hansson, which is incorporated herein by reference. At least a portion of the nicotinic compound can be employed in the form of a resin complex of nicotine, where nicotine is bound in an ion exchange resin, such as nicotine polacrilex. See, for example, U.S. Pat. No. 3,901,248 to Lichtneckert et al., which is incorporated herein by reference. At least a portion of the nicotine can be employed in the form of a salt. Salts of nicotine can be provided using the types of ingredients and techniques set forth in U.S. Pat. No. 2,033,909 to Cox et al. and U.S. Pat. No. 4,830,028 to Lawson et al., and Perfetti, *Beitrage Tabakforschung Int.,* 12: 43-54 (1983), which are incorporated herein by reference. See, also, U.S. patent application Ser. No. 12/769,335 to Brinkley et al., filed Apr. 28, 2010, which is incorporated herein by reference. Additionally, salts of nicotine have been available from sources such as Pfaltz and Bauer, Inc. and K&K Laboratories, Division of ICN Biochemicals, Inc.

Exemplary pharmaceutically acceptable nicotine salts include nicotine salts of tartrate (e.g., nicotine tartrate and nicotine bitartrate) chloride (e.g., nicotine hydrochloride and nicotine dihydrochloride), sulfate, perchlorate, ascorbate, fumarate, citrate, malate, lactate, aspartate, salicylate, tosylate, succinate, pyruvate, and the like; nicotine salt hydrates (e.g., nicotine zinc chloride monohydrate), and the like. Additional organic acids that can form salts with nicotine include formic, acetic, propionic, isobutyric, butyric, alpha-methylbutyric, isovaleric, beta-methylvaleric, caproic, 2-furoic, phenylacetic, heptanoic, octanoic, nonanoic, oxalic, malonic, and glycolic acid, as well as other fatty acids having carbon chains of up to about 20 carbon atoms.

In many embodiments, the nicotinic compound will be present in multiple forms. For example, the nicotine can be employed within the composition as a mixture of at least two salts (e.g., two different organic acid salts, such as a mixture of nicotine bitartrate and nicotine levulinate), as at least two salts that are segregated within the composition, in a free base form and salt form, in a free base form and a salt form that are segregated within the composition, in a salt form and in a complexed form (e.g., a resin complex such as nicotine polacrilex), in a salt for and in a complexed form that are segregated with in the composition, in a free base form and a complexed form, in a free base form and a complexed form that are segregated within the composition, or the like. As such, each single dosage unit or piece (e.g., gum piece, lozenge, sachet, film strip, etc.) can incorporate at least two forms of nicotine.

A nicotinic compound, in particular as compound such as nicotine, also can be employed in combination with other so-called tobacco alkaloids (i.e., alkaloids that have been identified as naturally occurring in tobacco). For example, nicotine, as employed in accordance with the present invention, can be employed in combination with nornicotine, anatabine, anabasine, and the like, and combinations thereof. See, for example, Jacob et al., *Am. J. Pub. Health,* 5: 731-736 (1999), which is incorporated herein by reference.

The compositions of the invention most preferably possess a form that is pharmaceutically effective and pharmaceutically acceptable. That is, the composition most preferably does not incorporate to any appreciable degree, or does not purposefully incorporate, significant amounts of components of tobacco, other than nicotine. As such, pharmaceutically effective and pharmaceutically acceptable compositions do not include tobacco in parts or pieces, processed tobacco components, or many of the components of tobacco traditionally present within tobacco-containing cigarettes, cigars, pipes, or smokeless forms of tobacco products.

Highly preferred compositions that are derived by extracting naturally-occurring nicotine from tobacco include less than 5 weight percent of tobacco components other than nicotine, more often less than about 0.5 weight percent, frequently less than about 0.25 weight percent, and typically are entirely absent or devoid of components of tobacco, processed tobacco components, or components derived from tobacco, other than nicotine, based on the total weight of the composition.

The pharmaceutical compositions of the invention may be conveniently made available in a unit dosage form, whereby formulations may be prepared by any of the methods generally known in the pharmaceutical arts. Such methods of preparation comprise combining (by various methods) an active agent with a suitable carrier or other adjuvant, which may consist of one or more ingredients. The combination of the active ingredient with the one or more adjuvants is then physically treated to provide the formulation in a suitable form for delivery (e.g., shaping into a lozenge or tablet).

The nicotine-containing pharmaceutical compositions of the invention can incorporate various pharmaceutically acceptable excipients. By "pharmaceutically acceptable excipient" is meant an excipient that can be used to facilitate the storage, administration, and/or the healing effect of an active agent (e.g., a nicotinic compound). The excipients are pharmaceutically acceptable in the sense of being compatible with the other ingredients of the formulation and not unduly deleterious to the recipient thereof; and they may also reduce any undesirable side effects of the active agent. See, Wang et al., *J. Parent. Drug Assn.*, 34(6): 452-462 (1980), which is incorporated herein by reference. Exemplary pharmaceutical excipients suitable for use in the compositions according to the invention are listed in Remington: *The Science & Practice of Pharmacy*, $21^{st}$ ed., Lippincott Williams & Wilkins (2006); in the *Physician's Desk Reference*, $64^{th}$ ed., Thomson P D R (2010); and in *Handbook of Pharmaceutical Excipients*, $6^{th}$ ed., Eds. Raymond C. Rowe et al., Pharmaceutical Press (2009), which are incorporated herein by reference.

The various excipients can vary, and the selection and amount of each excipient can depend upon factors such as the ultimate form and function of product that is desired. See, for example, the types of ingredients, relative amounts and combinations of ingredients, nicotine-containing formulations and preparation processes for nicotine-containing products set forth in U.S. Pat. No. 5,512,306 to Carlsson et al.; U.S. Pat. No. 5,525,351 to Dam; U.S. Pat. No. 5,549,906 to Santus; U.S. Pat. No. 5,711,961 to Reiner et al.; U.S. Pat. No. 5,811,126 to Krishnamurthy; U.S. Pat. No. 5,939,100 to Albrechtsen et al.; U.S. Pat. No. 6,024,981 to Khankari et al.; U.S. Pat. No. 6,083,531 to Humbert-Droz et al.; U.S. Pat. No. 6,090,401 to Gowan, Jr. et al.; U.S. Pat. No. 6,110,495 to Dam; U.S. Pat. No. 6,248,760 to Wilhelmsen; U.S. Pat. No. 6,280,761 to Santus; U.S. Pat. No. 6,426,090 to Ream et al.; U.S. Pat. No. 6,569,463 to Patel et al.; U.S. Pat. No. 6,583,160 to Smith et al.; U.S. Pat. No. 6,585,997 to Moro et al.; U.S. Pat. No. 6,676,959 to Andersson et al.; U.S. Pat. No. 6,893,654 to Pinney et al.; U.S. Pat. No. 7,025,983 to Leung et al. and U.S. Pat. No. 7,163,705 Johnson et al.; US Pat. Pub. Nos. 2003/0176467 to Andersson et al.; 2003/0235617 to Martino et al.; 2004/0096501 to Vaya et al.; 2004/0101543 to Liu et al.; 2004/0191322 to Hansson; 2005/0053665 to Ek et al.; 2005/0123502 to Chan et al.; 2008/0038209 to Andersen et al.; 2008/0286341 to Andersson et al.; 2009/0023819 to Axelsson; 2009/0092573 to Andersen; 2010/0004294 to Axelsson et al. and 2010/0061940 to Axelsson et al., which are incorporated herein by reference. See, also, U.S. patent application Ser. No. 12/769,335 to Brinkley et al., filed Apr. 28, 2010, which is incorporated herein by reference.

Representative types of excipients that are particularly useful for the manufacture of nicotine-containing products include fillers or carriers for active ingredients (e.g., calcium polycarbophil, microcrystalline cellulose, cornstarch, silicon dioxide or calcium carbonate), thickeners, film formers and binders (e.g., hydroxypropyl cellulose, hydroxypropyl methylcellulose, acacia, sodium alginate, xanthan gum and gelatin), buffers and pH control agents (e.g., magnesium oxide, magnesium hydroxide, potassium carbonate, sodium carbonate, potassium bicarbonate, sodium bicarbonate, or mixtures thereof), antiadherents (e.g., talc), glidants (e.g., colloidal silica), natural or artificial sweeteners (e.g., saccharin, acesulfame K, aspartame, sucralose, isomalt, lactose, mannitol, sorbitol, xylitol and sucrose), humectants (e.g., glycerin), preservatives and antioxidants (e.g., sodium benzoate and ascorbyl palmitate), surfactants (e.g., polysorbate 80), natural or artificial flavors (e.g., mint, cinnamon, cherry or other fruit flavors), dyes or pigments (e.g., titanium dioxide or D&C Yellow No. 10), and lubricants or processing aids (e.g, calcium stearate or magnesium stearate). Certain types of nicotine-containing products also can have outer coatings composed of ingredients capable of providing acceptable outer coatings (e.g., an outer coating can be composed of ingredients such as carnauba wax, and pharmaceutically acceptable forms of shellacs, glazing compositions and surface polish agents).

Representative compositions incorporating nicotine as an active ingredient can have various types of formats and configurations, and as a result, the character, nature, behavior, consistency, shape, form, size and weight of the composition can vary. The shape of a representative composition can be generally spherical, cylindrical (e.g., ranging form the general shape of a flattened disc to the general shape of a relatively long, slender stick), helical, obloid, square, rectangular, or the like; or the composition can have the form of a bead, granular powder, crystalline powder, capsule, film, strip, gel, or the like. The shape of the composition can resemble a wide variety of pill, tablet, lozenge, mini lozenge, capsule, caplet, microtab, pouch and gum types of products that traditionally have been employed for the administration of pharmaceutical types of products. The general nature of a representative composition can be soft or hard to the touch, or of intermediate softness or hardness; and as such, the composition can be considered to be malleable, flexible, chewy, resilient, brittle, or the like. When administered orally, various components of the product can be considered to be readily dispersible or slow to disperse, or those various components can dissolve at varying rates (e.g., from relatively fast to relatively slow). As a result, for compositions ingested by insertion in the mouth of the human subject, the release rate of active ingredient during use of the product can vary from relatively fast to relatively slow, depending upon factors such as the design of the product and the use of product by the subject using that product. See also, by way of example, the types of products proposed in U.S. Pat. No. 4,655,231 to Ray et al.; U.S. Pat. No. 5,147,654 to Place et al.; U.S. Pat. No. 5,543,424 to Carlsson et al.; U.S. Pat. No. 6,268,386 to Thompson; U.S. Pat. No. 6,319,510 to Yates; U.S. Pat. No. 6,488,953 Halliday et al.; U.S. Pat. No. 6,709,671 to Zerbe et al.; U.S. Pat. No. 7,025,983 to Leung et al.; U.S. Pat. No. 7,105,173 to Rolling; U.S. Pat. No. 7,115,297 to Stillman; U.S. Pat. No. 7,435,749 to Knight and U.S. Pat. No. 7,491,406 to Leung et al.; and US Pat. Pub. Nos. 2004/0191322 to Hansson;

2006/0198873 to Chan et al.; 2006/0240087 to Houze et al.; 2006/0204559 to Bess et al.; 2007/0269492 to Steen et al.; 2008/0020050 to Chau et al.; 2008/0286340 to Andersson et al.; 2008/0292683 to Sanghvi et al. and 2009/0004248 to Bunick et al., which are incorporated herein by reference.

Formulations of the present invention may include short-term, rapid-onset, rapid-offset, controlled release, sustained release, delayed release, and pulsatile release formulations, providing the formulations achieve administration of active ingredient. See, also, *Remington's Pharmaceutical Sciences*, 18$^{th}$ ed.; Mack Publishing Company, Eaton, Pa., (1990), which is incorporated herein by reference.

Solid dosage forms may be formulated so as to provide a delayed release of the active agent (i.e., the nicotinic compound), such as by application of a coating. Delayed release coatings are known in the art, and dosage forms containing such may be prepared by any known suitable method. Such methods generally involve application of a delayed release coating composition after preparation of the solid dosage form (e.g., a tablet or caplet). Application of the coating can be by methods such as airless spraying, fluidized bed coating, use of a coating pan, or the like. Materials for use as a delayed release coating can be polymeric in nature, such as cellulosic material (e.g., cellulose butyrate phthalate, hydroxypropyl methylcellulose phthalate, and carboxymethyl ethylcellulose), and polymers and copolymers of acrylic acid, methacrylic acid, and esters thereof.

Solid dosage forms according to the present invention may also be sustained release (i.e., releasing the active agent over a prolonged period of time), and may or may not also be delayed release. Sustained release formulations are known in the art and are generally prepared by dispersing the active ingredient within a matrix of a gradually degradable or hydrolyzable material, such as an insoluble plastic, a hydrophilic polymer, or a fatty compound. Alternatively, a solid dosage form may be coated with such a material.

The manners and methods used to formulate and manufacture the composition can vary. Typical conditions associated with manufacture of pharmaceutical types of products include control of heat and temperature (i.e., the degree of heat to which the various ingredients are exposed during manufacture and the temperature of the manufacturing environment), moisture content (e.g., the degree of moisture present within individual ingredients and within the final composition), humidity within the manufacturing environment, atmospheric control (e.g., nitrogen atmosphere), airflow experienced by the various ingredients during the manufacturing process, and other similar types of factors. Additionally, various process steps involved in product manufacture can involve selection of certain solvents and processing aids, use of heat and radiation, refrigeration and cryogenic conditions, ingredient mixing rates, and the like. The manufacturing conditions also can be controlled due to selection of the form of various ingredients (e.g., solid, liquid, or gas), particle size or crystalline nature of ingredients of solid form, concentration of ingredients in liquid form, or the like. Ingredients can be processed into the desired composition by techniques such as extrusion, compression, spraying, and the like.

A carrier and a non-active ingredient are combined to form an intimate mixture that is employed as an excipient in accordance with the present invention. The non-active ingredient most preferably is a material that possesses the ability to alter the pH of the biological system with which it is administered. The carrier for that non-active material can vary. The carrier most preferably is a porous particulate carrier material, such as a microcrystalline cellulosic material, silica, or calcium silicate. Examples of microcrystalline cellulose materials are those that have been available under the tradenames Avicel from FMC Corporation (e.g., grades DG, CE-15, HFE-102, PH-100, PH-102, PH-103, PH-105, PH-112, PH-113, PH-200, PH-300 and PH-302); Vivapur from JRS PHARMA GmbH & Co. KF (e.g., grades 12, 14, XLM200, 101, 102, 103, 105, 112, 200, 301 and 302); Vivacel from J. Rettenmaier & Sohne GmbH (e.g., grades 12, 20, 101 and 102) and Emocel from JRS PHARMA GmbH & Co. KF (e.g., grades 50M, 90M, LM50, XLM90, HD90 and LP200). See also, for example, the types of microcrystalline materials set forth in US Pat. Pub. No. 2004/0191322 to Hansson and EP 1578422 to Hansson, which are incorporated herein by reference. The particle sizes of the porous particulate carrier materials (e.g., microcrystalline cellulose) can vary, and certain representative materials have particle sizes in the range of about 15 microns to about 250 microns in diameter.

The non-active ingredient is a composition that is different in chemical structure from the active ingredient with which it is combined to provide a therapeutic composition in accordance with the present invention. In certain embodiments, the non-active ingredient is a base or a buffering agent that buffers in a basic pH range or a combination thereof. In other embodiments, the non-active ingredient is an acid or a buffering agent that buffers in an acidic pH range or a combination thereof.

The non-active ingredient basic substance can vary. Exemplary strong bases are sodium hydroxide, potassium hydroxide, and mixtures thereof. Exemplary weak bases are sodium carbonate, potassium carbonate, sodium bicarbonate, potassium bicarbonate, and mixtures thereof. See, also, the various types of buffering agents that are set forth in EP 1458388 to Lindell et al., which is incorporated herein by reference. The non-active ingredient that is combined in intimate contact with the carrier (e.g., sorbed onto a porous particulate material such as microcrystalline cellulose) can be employed as a single ingredient (e.g., as sodium hydroxide or as sodium bicarbonate) or as a combination of at least two ingredients (e.g., as a mixture of sodium carbonate and sodium bicarbonate). In addition, the non-active ingredient that is combined in intimate contact with the carrier (e.g., sorbed onto a material such as microcrystalline cellulose) can be employed as a single buffering ingredient (e.g., as sodium dihydrogen phosphate) or as a combination of at least two ingredients (e.g., as a mixture of sodium carbonate and sodium dihydrogen phosphate).

The non-active ingredient acidic substance can vary. Exemplary acidic materials include citric acid, malic acid, oxalic acid, levulinic acid, and mixtures thereof. Exemplary buffering agents include sodium citrate, sodium acetate, monopotassium phosphate, and the like. The non-active ingredient that is combined in intimate contact with the carrier (e.g., sorbed onto a porous material such as microcrystalline cellulose) can be employed as a single ingredient (e.g., as citric acid or as malic acid) or as a combination of at least two ingredients (e.g., as a mixture of malic acid and citric acid). In addition, the non-active ingredient that is combined in intimate contact with the carrier (e.g., sorbed onto a material such as microcrystalline cellulose) can be employed as a single buffering ingredient (e.g., as sodium citrate) or as a combination of at least two ingredients (e.g., as a mixture of sodium citrate and citric acid).

The amount of non-active ingredient (e.g., basic material and/or buffering agent, or acidic material and/or buffering agent) that is sorbed on the carrier or substrate material can vary. Typically, the substrate material (i.e., the porous particulate carrier material) that acts as a carrier for the basic material and/or buffering agent (or acidic material and/or buffering agent) is the predominant component, by weight, of the resulting mixture. Typically, the substrate material comprises at least about 70 percent, usually at least about 80 percent, often at least about 90 percent, and frequently at least about 95 percent, of the weight of the mixture, based on the combined weight of the substrate material and the basic material and/or buffering agent (or the combined weight of the substrate material and the acidic material and/or buffering agent); while the amount of basic material and/or buffering agent typically comprises up to about 30 percent, usually at least about 20 percent, often up to about 10 percent, and frequently up to about 5 percent, of the weight of the mixture, based on the combined weight of the substrate material and the basic material and/or buffering agent (or the combined weight of the substrate material and the acidic material and/or buffering agent).

The manner by which the non-active ingredient basic material and/or buffering agent (or acidic material and/or buffering agent) is sorbed on the substrate material can vary. For example, the intimate admixture of ingredients can be produced using suitably modified techniques of the type set forth in US Pat. Appl. Pub. No. 2004/0191322 to Hansson, which is incorporated herein by reference. Typically, the non-active ingredient is dissolved or dispersed in a suitable liquid (e.g., various solvents such as a liquid having an aqueous character, a water/ethanol solution, or the like), the liquid solution or dispersion and particulate carrier material are contacted with one another, and the liquid is removed (e.g., by spray drying, vacuum drying, air drying, heating, or the like) so as to provide a solid material. It is highly preferred that the resulting intimate mixture of non-active ingredient and particulate carrier not incorporate (i.e., be virtually absent of) the active ingredient with which the intimate mixture is intended to be combined during the formulation of the final therapeutic composition.

A particularly suitable method for producing a mixture of non-active ingredient basic substance and/or buffering agent sorbed onto a porous substrate involves providing a solution of basic substance and/or buffering agent in a liquid solvent to provide a solution, providing the porous substrate material, combining the substrate material and liquid solution, and removing the solvent of the resulting mixture to provide a dry solid mixture. The liquid typically is a liquid having an aqueous character. Often, the liquid solution and the substrate that are combined can be subjected to mixing and/or heating slightly above ambient conditions. Typically, liquid can be applied to the substrate using spraying techniques. Additionally, it is desirable to agitate, tumble, shake or otherwise mix (e.g., using pan coaters, tumbling mixers, shear agitators, or the like) the substrate while the liquid solution and the substrate are being contacted with one another, in order to assist in providing uniform application of the liquid solution to the substrate. Often, the removal of the liquid can be provided by drying techniques, and the mixture can be heated to temperatures slightly above ambient during drying.

In certain embodiments, the mixture of porous carrier and sorbed non-active ingredient can be further processed prior to incorporation into a nicotine-containing composition. For example, a coating material can be applied to the mixture in order to provide a protective barrier to enhance storage stability, to change the dissolution or absorption properties of the sorbed non-active material when ingested, and the like. Exemplary coating materials include acrylic polymer compositions such as those available under the tradename EUDRAGIT® available from Evonik Industries AG.

The manners and methods for incorporating the excipient material (e.g., a material composed of an intimate mixture of microcrystalline cellulose and basic material and/or buffering agent) into the nicotine-containing composition can vary. The location of the excipient material within the nicotine-containing composition can also vary. The excipient material can be located throughout the therapeutic composition or formulation, or in selected regions of the formulation (e.g., homogeneously throughout the composition, in an outer coating of the composition or in the region of the composition occupied by nicotine or in selected layer(s) of a laminated composition). As such, certain regions of the formulation can be essentially devoid of the excipient material, or there can exist a concentration gradient of excipient material within or throughout the formulation, or a certain region of the formulation can have a relatively high concentration of excipient material relative to other regions of that formulation. Nicotine-containing compositions can be co-extruded, laminated or formed so as to have sandwich-type forms; and hence the location of nicotine, excipient material and other ingredients can be controlled in order to provide the desired features such as performance, behavior, interaction or non-interaction with other ingredients, storage stability, and the like. In addition, mixtures of component ingredients can be formulated and manufactured into core/shell types of configurations (e.g., gum or lozenge types of products that have an inner region and at least one additional overlayer), with the various regions of such products having differing overall compositions or properties. Thus, for example, the excipient material can have a relatively high concentration towards the inner region of the product, or a relatively high concentration towards the outer region of the product.

In use, the compositions of the present invention are typically administered in a form adapted for buccal, sublingual, or nasal delivery. In certain embodiments, the compositions are in a form particularly suitable for oral ingestion. For example, nicotine-containing compositions can be administered and employed using the manners and methods typically used for the administration of traditional types of nicotine-containing gums, lozenges and pouch products, and though much less preferred, sprays.

One particularly preferred type of a representative composition incorporating nicotine as an active ingredient, and that provides nicotine in a non-inhalable form, has the form of a gum or other type of similarly chewable product. Gum forms of product include gum base (e.g., typically the types of pharmaceutically acceptable gum bases available from sources such as Gum Base Co. S.p.a., Wm. J. Wrigley Jr. Company or Gumlink A/S). See, for example, the types of nicotine-containing gums, gum formulations, gum formats and configurations, gum characteristics and techniques for formulating or manufacturing gums set forth in U.S. Pat. No. 3,845,217 to Ferno et al.; U.S. Pat. No. 3,877,468 to Lichtneckert et al.; U.S. Pat. No. 3,901,248 to Lichtneckert et al.; U.S. Pat. No. 5,154,927 to Song et al.; U.S. Pat. No. 6,322,806 to Ream et al.; U.S. Pat. No. 6,344,222 to Cherukuri et al.; U.S. Pat. No. 6,355,265 to Ream et al.; U.S. Pat. No. 6,358,060 to Pinney et al.; U.S. Pat. No. 6,773,716 to Ream et al.; U.S. Pat. No. 6,893,654 to Pinney et al.; U.S. Pat. No. 7,101,579 Athanikar et al.; U.S. Pat. No. 7,163,705 to Johnson et al. and U.S. Pat. No. 7,208,186 to Norman et al.; US Pat. Pub. Nos. 2004/0194793 to Lindell et al.; 2006/0099300 to Andersen et al.; 2006/0121156 to Andersen et al.; 2006/0165842 to Andersen et al.; 2006/0204451 to Salini; 2006/0246174 to Andersen et al.; 2006/0275344 to Mody et al.; 2007/0014887 to Cherukuri et al.; 2007/0269386 to Steen et al.; 2009/0092573 to Andersen and 2010/0061940 to Axelsson et al.; which are incorporated herein by reference. The amount of composition contained within each piece or unit of gum type of product can vary. For example, a representative unit for gum products generally weighs at least about 0.5 g, often at least about 1 g, and frequently at least about 1.5 g; while the weight of a representative unit for such products generally does not exceed about 3 g, often does not exceed about 2.5 g, and frequently does not exceed about 2 g. The time period over which a gum piece can be chewed can vary; and typically, each piece of gum is chewed for at least about 5 minutes, often at least about 10 minutes, while each piece of gum typically is chewed for up to about 40 minutes, often up to about 30 minutes.

Another particularly preferred type of a representative composition incorporating nicotine as an active ingredient, and that provides nicotine in a non-inhalable form, has the form of a lozenge, mini lozenge, tablet, microtab, or other tablet-type product. See, for example, the types of nicotine-containing lozenges, lozenge formulations, lozenge formats and configurations, lozenge characteristics and techniques for formulating or manufacturing lozenges set forth in U.S. Pat. No. 4,967,773 to Shaw; U.S. Pat. No. 5,110,605 to Acharya; U.S. Pat. No. 5,733,574 to Dam; U.S. Pat. No. 6,280,761 to Santus; U.S. Pat. No. 6,676,959 to Andersson et al.; U.S. Pat. No. 6,248,760 to Wilhelmsen and U.S. Pat. No. 7,374,779 to Chen et al.; US Pat. Pub. Nos. 2001/0016593 to Wilhelmsen; 2004/0101543 to Liu et al.; 2006/0120974 to Mcneight; 2008/0020050 to Chau et al.; 2009/0081291 to Gin et al. and 2010/0004294 to Axelsson et al.; and PCT WO 91/09599 to Carlsson et al., which are incorporated herein by reference. The amount of the composition of the invention contained within each piece or unit of lozenge type of product can vary. For example, a representative unit for lozenge products generally weighs at least about 100 mg, often at least about 200 mg, and frequently at least about 300 mg; while the weight of a representative unit for such products generally does not exceed about 1.5 g, often does not exceed about 1 g, and frequently does not exceed about 0.75 g.

Another particularly preferred type of a representative composition incorporating nicotine as an active ingredient, and that provides nicotine in a non-inhalable form, has the form of a pouch or sachet type of product. See, for example, the types of pouch materials and nicotine-containing formulations set forth in US Pat. Pub. No. 2009/0293895 to Axelsson et al., which is incorporated herein by reference. See also, for example, the types of pouch materials and pouch manufacturing techniques (e.g., pouch filling and sealing techniques) set forth in US Pat. Pub. No. 2010/0018539 to Brinkley et al., which is incorporated herein by reference. The amount of composition contained within each pouch can vary. For example, a representative pouch product generally contains at least about 75 mg, often at least about 100 mg, and frequently at least about 150 mg, of composition according to the invention; while the amount of composition contained in a single representative pouch generally does not exceed about 500 mg, often does not exceed about 400 mg, and frequently does not exceed about 300 mg.

The amount of active ingredient within the overall composition can vary. For a composition intended for oral consumption by insertion into the mouth of the subject (e.g., chewable piece of gum product, a lozenge, a pouch product, or the like), the amount of nicotine within each dosage piece or unit typically is at least about 0.5 mg, generally is at least 1 mg, often is at least about 1.5 mg, and frequently is at least about 2 mg; while the amount of nicotine within each piece typically does not exceed about 10 mg, generally does not exceed about 8 mg, often does not exceed about 6 mg, and frequently does not exceed about 5 mg, calculated as nicotine base. Exemplary types of such products can incorporate about 2 mg, about 2.5 mg, about 3 mg, about 3.5 mg and about 4 mg of nicotine per piece or unit, calculated as nicotine base.

Another type of a representative composition incorporating nicotine as an active ingredient has the form of a spray. Typically, such sprays are applied within the nose or mouth for absorption through nasal or oral mucosa, as opposed to a vapor or fine aerosol that is inhaled into the lungs. See, for example, the types of spray materials and nicotine-containing spray formulations set forth in U.S. Pat. No. 4,579,858 to Ferno et al.; U.S. Pat. No. 5,656,255 to Jones; U.S. Pat. No. 6,024,097 to Von Wielligh and U.S. Pat. No. 6,596,740 to Jones; US Pat. Pub. Nos. 2003/0159702 to Lindell et al.; 2007/0163610 to Lindell et al. and 2009/0023819 to Axelsson; EP 1458388 to Lindell et al.; and PCT WO 2008/037470 to Axelsson et al., which are incorporated herein by reference. Preferred spray products produce sprays or mists using nebulizers or other types of devices for producing aerosols by mechanical means. Preferred spray products employ liquid solvents or carriers (e.g., water or water/ethanol mixtures) that contain nicotine and the intimate mixture of basic material and particulate carrier; and it is highly preferred that those formulations be well shaken or otherwise agitated prior to use. The concentration of the nicotine within the liquid spray formulation can vary, but typically is in the range of about 0.5 percent to about 5 percent, often about 1 percent to about 3 percent, based on the total weight of the liquid formulation and calculated as nicotine base.

Although the compositions of the invention are preferably non-inhalable, it is possible to formulate the above-noted combinations of a nicotinic compound and an intimate mixture of particulate carrier and non-active ingredient basic material and/or buffering agent in a form capable of pulmonary delivery using various types of inhalation devices and vapor delivery systems designed to deliver an active agent to the lungs as opposed to buccal, sublingual, or nasal delivery. See, for example, the types of inhalable formulations and vapor delivery devices and systems set forth in U.S. Pat. No. 4,284,809 to Ray; U.S. Pat. No. 4,800,903 to Ray et al.; U.S. Pat. No. 5,167,242 to Turner et al.; U.S. Pat. No. 6,098,632 to Turner et al.; U.S. Pat. No. 6,234,169 to Bulbrook et al. and U.S. Pat. No. 6,874,507 to Fan; US Pat. Pub. Nos. 2004/0034068 to Warchol et al; 2006/0018840 to Lechuga-Ballesteros; 2008/0302375 to Andersson et al. and 2009/0005423 to Gonda; and EP 1618803 to Hon, which are incorporated herein by reference.

The dose of active ingredient (i.e., all the various nicotine forms) is that amount effective to treat some symptoms of or prevent occurrence of the symptoms of, the condition, disease, or disorder from which the subject or patient suffers. By "effective amount", "therapeutic amount" or "effective dose" is meant that amount sufficient to elicit the desired pharmacological or therapeutic effects, thus resulting in effective prevention or treatment of the condition, disease, or disorder. Thus, an effective amount of active ingredient is an amount sufficient to enter relevant regions of the body (e.g., including passing across the blood-brain barrier of the subject), to bind to relevant receptor sites in the CNS and PNS of the subject, and/or to elicit neuropharmacological effects (e.g., elicit neurotransmitter secretion, thus resulting in effective prevention or treatment of the condition, disease, or disorder). Prevention of the disorder is manifested, for example, by delaying the onset of the symptoms of the condition, disease, or disorder. Treatment of the disorder is manifested by, for example, a decrease in the symptoms associated with the condition, disease, or disorder or an amelioration of the reoccurrence of the symptoms thereof.

For compositions of the present invention, the intended daily dose of the active ingredient can vary. The overall dose of active ingredient can depend upon factors such as the weight of the subject ingesting the composition, the type of condition, disease, or disorder being treated, the state or severity of the condition, disease, or disorder being treated, the desired pharmacological effect, or other such factors. Typically, the amount of nicotine active ingredient, calculated as nicotine base, administered to a subject per day is at least about 2 mg, often is at least about 4 mg, and frequently is at least about 10 mg. Typically, the amount of nicotine active ingredient administered to a subject per day does not exceed about 60 mg, often does not exceed about 50 mg, and frequently does not exceed about 40 mg. See also, for example, the types of dosing regimens and administration techniques set forth in U.S. Pat. No. 5,593,684 to Baker et al. and U.S. Pat. No. 6,660,754 to Kyle et al.; and US Pat. Pub. Nos. 2004/0006113 to Sachs; 2005/0214229 to Pinney et al.; 2008/0124283 to Andersen and 2009/0293895 to Axelsson et al.; which are incorporated herein by reference.

The compositions of the present invention can be used for treatment of a wide variety of conditions, diseases, and disorders responsive to stimulation of one or more types of nicotinic acetylcholinergic receptors (nAChRs). The compositions can be used to treat those types of conditions, diseases, and disorders that have been reported to be treatable through the use or administration of nicotine as an agonist of nAChRs, such as neurodegenerative diseases, behavioral disorders, cognitive disorders and cognitive affective disorders. As such, the compositions can be used to treat various CNS conditions, diseases, and disorders, and the compositions also can be used as nicotine-containing products, such as smoking cessation aids (i.e., as components of NRT).

The following examples are illustrative of representative examples of the present invention that can be employed to provide for oral ingestion of nicotine for therapeutic purposes, such as NRT, but the examples should not be construed as limiting the scope of the present invention.

Example 1

About 180 ml of deionized water is provided at room temperature. Into that water is dissolved about 20 gm of sodium hydroxide. As such, an aqueous solution of 10 percent sodium hydroxide is obtained.

Commercially available microcrystalline cellulose is obtained. The microcrystalline cellulose is available under the tradename Vivapur 101 from JRS PHARMA GmbH & Co. KF. About 9.9 g of the microcrystalline cellulose in dry form is provided at room temperature, and to that dry particulate is applied by spraying, about 1 gm of the 10 percent sodium hydroxide solution. The sodium hydroxide solution is sprayed onto the dry particulate using a Nalgene Aerosol Spray Bottle Cat. No. 2430-0200 while the particulate is subjected to mixing, and as such the solution is evenly applied to the particulate. Then, the mixture is air dried at room temperature to yield a dry product having a weight of about 10 gm. The resulting first sample of microcrystalline cellulose and sodium hydroxide intimate admixture is white in color, is composed of about 99 parts microcrystalline cellulose and about 1 part sodium hydroxide, and is a dry, free-flowing, fine powdery material. The resulting representative excipient is essentially pure (i.e., the intimate mixture is composed of microcrystalline cellulose and sodium hydroxide, and is virtually absent of other excipient materials and of active ingredient of a therapeutic composition with which that excipient may be combined). The representative excipient can be easily handled (e.g., for storage, weighing, mixing, and the like) for use as an excipient, and can be used in combination with other excipients and in combination with active ingredient components of therapeutic compositions.

A second sample composed of microcrystalline cellulose material is prepared in generally the same manner used to provide the first sample, except that about 9.8 gm of the microcrystalline cellulose has about 2 gm of the previously described sodium hydroxide solution applied thereto. The resulting second sample of microcrystalline cellulose and sodium hydroxide material is white in color, is composed of about 98 parts microcrystalline cellulose and about 2 parts sodium hydroxide, and is a dry, free-flowing, fine powdery material.

The pH of 50 ml of deionized water is measured at room temperature using a Fisher Science Education pH Meter 510 Series, and the pH of the water is determined to be 6.93.

About 2.5 gm of the microcrystalline cellulose is incorporated into about 50 ml of deionized water, and the pH of that liquid mixture is measured after about 1 minute after mixing. The pH of the resulting mixture, at room temperature, is determined to be 5.96.

About 2.5 gm of the first sample of microcrystalline cellulose and sodium hydroxide is incorporated into about 50 ml of deionized water, and the pH of that liquid mixture is measured after about 1 minute after mixing. The pH of the resulting mixture, at room temperature, is determined to be 11.01.

About 2.5 gm of the second sample of microcrystalline cellulose and sodium hydroxide is incorporated into about 50 ml of deionized water, and the pH of that liquid mixture is measured after about 1 minute after mixing. The pH of the resulting mixture, at room temperature, is determined to be 11.12.

A solution of levulinic acid in water is provided. Sufficient levulinic acid is added to deionized water at room to temperature to provide an aqueous solution containing about 1 percent levulinic acid. The pH of that solution is measured at room temperature, and is determined to be 3.28

About 2.5 gm of the microcrystalline cellulose is incorporated into about 50 ml of the aforementioned aqueous levulinic acid solution, and the pH of that liquid mixture is measured after about 1 minute after mixing. The pH of the resulting mixture, at room temperature, is determined to be 3.33.

About 2.5 gm of the aforementioned first sample of microcrystalline cellulose and sodium hydroxide is incorporated into about 50 ml of the aforementioned aqueous levulinic acid solution, and the pH of that liquid mixture is measured after about 1 minute after mixing. The pH of the resulting mixture, at room temperature, is determined to be 9.00.

About 2.5 gm of the aforementioned second sample of microcrystalline cellulose and sodium hydroxide is incorporated into about 50 ml of the aforementioned aqueous levulinic acid solution, and the pH of that liquid mixture is measured after about 1 minute after mixing. The pH of the resulting mixture, at room temperature, is determined to be 10.04.

Example 2

About 180 ml of deionized water is provided at room temperature. Into that water is dissolved about 20 gm of sodium carbonate. As such, an aqueous solution of 10 percent sodium carbonate is obtained.

Commercially available microcrystalline cellulose is obtained. The microcrystalline cellulose is available under the tradename Vivapur 101 from JRS PHARMA GmbH & Co. KR About 9.5 g of the microcrystalline cellulose in dry form is provided at room temperature, and to that dry particulate is applied by spraying, about 5 gm of the 10 percent sodium carbonate solution. The sodium carbonate solution is sprayed onto the dry particulate using a Nalgene Aerosol Spray Bottle Cat. No. 2430-0200 while the particulate is subjected to mixing, and as such the solution is evenly applied to the particulate. Then mixture is dried at room temperature to yield a dry product having a weight of about 10 gm. The resulting sample of microcrystalline cellulose and sodium carbonate intimate admixture is white in color, is composed of about 95 parts microcrystalline cellulose and about 5 parts sodium carbonate, and is a dry, free-flowing, fine powdery material. The resulting representative excipient is essentially pure (i.e., the intimate mixture is composed of microcrystalline cellulose and sodium carbonate, and is virtually absent of other excipient materials and of active ingredient of a therapeutic composition with which that excipient may be combined).

Example 3

About 180 ml of deionized water is provided at room temperature. Into that water is dissolved about 20 gm of citric acid. As such, an aqueous solution of 10 percent citric acid is obtained.

Commercially available microcrystalline cellulose is obtained. The microcrystalline cellulose is available under the tradename Vivapur 101 from JRS PHARMA GmbH & Co. KF. About 9.5 g of the microcrystalline cellulose in dry form is provided at room temperature, and to that dry particulate is applied by spraying, about 5 gm of the 10 percent citric acid solution. The citric acid solution is sprayed onto the dry particulate using a Nalgene Aerosol Spray Bottle Cat. No. 2430-0200 while the particulate is subjected to mixing, and as such the solution is evenly applied to the particulate. Then the resulting mixture is dried at room temperature to yield a dry product having a weight of about 10 gm. The resulting sample of microcrystalline cellulose and citric acid intimate admixture is white in color, is composed of about 95 parts microcrystalline cellulose and about 5 parts citric acid, and is a dry, free-flowing, fine powdery material. The resulting representative excipient is essentially pure (i.e., the intimate mixture is composed of microcrystalline cellulose and citric acid, and is virtually absent of other excipient materials and of active ingredient of a therapeutic composition with which that excipient may be combined).

Example 4

About 180 ml of deionized water is provided at room temperature. Into that water is dissolved equal amounts of sodium carbonate and sodium bicarbonate (i.e., about 10 gm of sodium carbonate and 10 gm of sodium bicarbonate). As such, an aqueous solution of 5 percent sodium carbonate and 5 percent sodium bicarbonate is obtained.

Commercially available microcrystalline cellulose is obtained. The microcrystalline cellulose is available under the tradename Vivapur 101 from JRS PHARMA GmbH & Co. KF. About 9.5 g of the microcrystalline cellulose in dry form is provided at room temperature, and to that dry particulate is applied by spraying, about 5 gm of the sodium carbonate/sodium bicarbonate aqueous solution. The solution is sprayed onto the dry particulate using a Nalgene Aerosol Spray Bottle Cat. No. 2430-0200 while the particulate is subjected to mixing, and as such the solution is evenly applied to the particulate. Then the resulting mixture is dried at room temperature to yield a dry product having a weight of about 10 gm. The resulting sample of microcrystalline cellulose, sodium bicarbonate and sodium carbonate intimate admixture is white in color, is composed of about 95 parts microcrystalline cellulose, about 2.5 parts sodium bicarbonate and about 2.5 parts sodium carbonate, and is a dry, free-flowing, fine powdery material. The resulting representative excipient is essentially pure (i.e., the intimate mixture is composed of microcrystalline cellulose, sodium bicarbonate and sodium carbonate, and is virtually absent of other excipient materials and of active ingredient of a therapeutic composition with which that excipient may be combined).

Example 5

About 180 ml of deionized water is provided at room temperature. Into that water is dissolved about 20 gm of trisodium phosphate. As such, an aqueous solution of 10 percent trisodium phosphate is obtained.

Commercially available microcrystalline cellulose is obtained. The microcrystalline cellulose is available under the tradename Vivapur 101 from JRS PHARMA GmbH & Co. KF. About 9 g of the microcrystalline cellulose in dry form is provided at room temperature, and to that dry particulate is applied by spraying, about 10 gm of the 10 percent trisodium phosphate solution. The trisodium phosphate solution is sprayed onto the dry particulate using a Nalgene Aerosol Spray Bottle Cat. No. 2430-0200 while the particulate is subjected to mixing, and as such the solution is evenly applied to the particulate. Then the resulting mixture is dried at room temperature to yield a dry product having a weight of about 10 gm. The resulting sample of microcrystalline cellulose and trisodium phosphate intimate admixture is white in color, is composed of about 90 parts microcrystalline cellulose and about 10 parts trisodium phosphate, and is a dry, free-flowing, fine powdery material. The resulting representative excipient is essentially pure (i.e., the intimate mixture is composed of microcrystalline cellulose and trisodium phosphate, and is virtually absent of other excipient materials and of active ingredient of a therapeutic composition with which that excipient may be combined).

Example 6

A gum generally similar in shape and form to a nicotine-containing gum incorporating 4 mg of nicotine and commercially available as Nicorette Original Gum (distributed by GlaxoSmithKline Consumer Healthcare, L.P.) is produced using generally similar active ingredient (e.g., nicotine polacrilex) and generally excipient ingredients used for the manufacture of the commercial gum (e.g., colorant, flavors, glycerin, gum base and sorbitol), except that the sodium carbonate within the nicotine-containing gum is replaced by the microcrystalline cellulose/sodium carbonate mixture that is prepared in accordance with Example 2. Sufficient microcrystalline cellulose/sodium carbonate mixture is incorporated into the nicotine-containing gum such that the amount of sodium carbonate within the nicotine-containing gum from the microcrystalline/sodium carbonate mixture is equal to that amount of sodium carbonate that would be originally present within the original formulation of unmodified, commercial nicotine-containing gum. As such, there is provided in the form of a gum a composition incorporating an active ingredient and a non-active ingredient in intimate contact with a microcrystalline cellulose carrier material.

Example 7

A coated gum generally similar in shape and form to a nicotine-containing gum incorporating 4 mg of nicotine and commercially available as Coated Nicotine Gum (distributed by Walgreen Co.) is produced using generally similar active ingredient (e.g., nicotine polacrilex) and generally excipient ingredients used for the manufacture of the commercial gum (e.g., acacia, acesulfame, potassium, carnuba wax, colorant, flavors, gum base, hydroxypropyl cellulose, magnesium oxide, sodium bicarbonate, talc, titanium dioxide and xylitol), except that the sodium carbonate within the nicotine-containing gum is replaced by the microcrystalline cellulose/sodium carbonate mixture that is prepared in accordance with Example 2. Sufficient microcrystalline cellulose/sodium carbonate mixture is incorporated into the nicotine-containing gum such that the amount of sodium carbonate within the nicotine-containing gum from the microcrystalline/sodium carbonate mixture is equal to that amount of sodium carbonate that would be originally present within the original formulation of unmodified, commercial nicotine-containing gum.

Example 8

A coated gum generally similar in shape and form to a nicotine-containing gum incorporating 4 mg of nicotine and commercially available as Zonnic (distributed by Niconovum AB) is produced using generally similar excipient ingredients used for the manufacture of the commercial gum, except that except that the sodium carbonate within the nicotine-containing gum is replaced by the microcrystalline cellulose/sodium carbonate mixture that is prepared in accordance with Example 2. Sufficient microcrystalline cellulose/sodium carbonate mixture is incorporated into the nicotine-containing gum such that the amount of sodium carbonate within the nicotine-containing gum from the microcrystalline/sodium carbonate mixture is equal to that amount of sodium carbonate that would be originally present within the original formulation of unmodified, commercial nicotine-containing gum.

Example 9

A lozenge generally similar in shape and form to a nicotine-containing lozenge incorporating 2 mg of nicotine and commercially available as Nicotine Polacrilex Lozenge (distributed by CVS Pharmacy, Inc.) is produced using generally similar excipient ingredients used for the manufacture of the commercial lozenge, except that the sodium carbonate within the nicotine-containing lozenge is replaced by the microcrystalline cellulose/sodium carbonate mixture that is prepared in accordance with Example 2. Sufficient microcrystalline cellulose/sodium carbonate mixture is incorporated into the nicotine-containing lozenge such that the amount of sodium carbonate within the nicotine-containing lozenge from the microcrystalline/sodium carbonate mixture is equal to that amount of sodium carbonate that would be originally present within the original formulation of unmodified, commercial nicotine-containing lozenge. As such, there is provided in the form of a lozenge a composition incorporating an active ingredient and a non-active ingredient in intimate contact with a microcrystalline cellulose carrier material.

Example 10

A lozenge generally similar in shape and form to a nicotine-containing lozenge incorporating 2.5 mg of nicotine is produced using generally similar excipient ingredients and processing conditions used for the manufacture of that lozenge set forth in Table 1 of Example 3 of US Pat. Pub. No. 2010/0004294 to Axelsson et al., except that the sodium carbonate within the nicotine-containing lozenge is replaced by the microcrystalline cellulose/sodium carbonate mixture that is prepared in accordance with Example 2. Sufficient microcrystalline cellulose/sodium carbonate mixture is incorporated into the nicotine-containing lozenge such that the amount of sodium carbonate within the nicotine-containing lozenge from the microcrystalline/sodium carbonate mixture is equal to that amount of sodium carbonate that would be originally present within the original formulation of unmodified nicotine-containing lozenge of the cited example of the patent reference.

Example 11

A lozenge generally similar in shape and form to a nicotine-containing lozenge incorporating 2.5 mg of nicotine is produced using generally similar excipient ingredients and processing conditions used for the manufacture of that lozenge set forth in Table 1 of Example 3 of US Pat. Pub. No. 2010/0004294 to Axelsson et al., except that the sodium carbonate within the nicotine-containing lozenge is replaced by the microcrystalline cellulose/sodium carbonate mixture that is prepared in accordance with Example 2. Sufficient microcrystalline cellulose/sodium carbonate mixture is incorporated into the nicotine-containing lozenge such that the amount of sodium carbonate within the nicotine-containing lozenge from the microcrystalline/sodium carbonate mixture is equal to that amount of sodium carbonate that would be originally present within the original formulation of unmodified nicotine-containing lozenge of the cited example of the patent reference.

In addition, prior to being contacted with the other ingredients of the lozenge to form the lozenge, the microcrystalline cellulose/sodium carbonate mixture is coated with a solution of the EUDRAGIT® L100 coating material dissolved in ethanol and dried, using the manner generally set forth in the cited example of the patent reference. As such, the lozenge contains a nicotine salt active ingredient sorbed onto microcrystalline cellulose, and a separate ingredient in the form of a coated excipient composed of sodium carbonate sorbed onto microcrystalline cellulose.

Example 12

A pouch type of product similar in shape and form to a nicotine-containing pouch commercially available as Zonnic (distributed by Niconovum A.B.) is produced using generally similar pouch material, active ingredient and excipient ingredients used for the manufacture of the commercial pouch, except that the except that the trisodium phosphate of the pouch type product replaced by the microcrystalline cellulose/trisodium phosphate mixture that is prepared in accordance with Example 5. Sufficient microcrystalline cellulose/trisodium phosphate mixture is incorporated into the nicotine-containing pouch type product such that the amount of trisodium phosphate within the nicotine-containing pouch type product from the microcrystalline/trisodium phosphate mixture is equal to that amount of trisodium phosphate that would be originally present within the original formulation of unmodified, commercially available nicotine-containing pouch type product.

Example 13

Pouch type products generally similar in shape and form to a nicotine-containing pouches set forth as snuff bag composition J in Example 1 of PCT WO 2007/104573 to Axelsson et al. are produced using generally similar excipient ingredients used for the manufacture of those pouch type products, except that the sodium carbonate and sodium bicarbonate within the disclosed is replaced by the microcrystalline cellulose/sodium carbonate/sodium bicarbonate mixture that is prepared in accordance with Example 4. Sufficient microcrystalline cellulose/sodium carbonate/bicarbonate mixture is incorporated into the nicotine-containing pouch type product such that the amount of sodium carbonate and sodium bicarbonate within the nicotine-containing pouch type product from the microcrystalline/sodium carbonate/sodium bicarbonate mixture is equal to that amount of sodium carbonate and sodium bicarbonate that would be originally present within the original formulation of unmodified nicotine-containing pouch type product of the cited example of the patent reference.

What is claimed is:

1. A nicotine-containing pharmaceutical composition, comprising:
    at least one source of nicotine; and
    a mixture of a porous particulate carrier and at least one non-active ingredient sorbed onto the porous particulate carrier, the non-active ingredient being in the form of a base or a buffering agent,
    wherein the at least one non-active ingredient comprises sodium carbonate, sodium bicarbonate, a combination of sodium carbonate and sodium bicarbonate, or trisodium phosphate, and the porous particulate carrier comprises microcrystalline cellulose;
    wherein the composition is in a pharmaceutically acceptable form adapted for oral or nasal delivery of the composition; and
    wherein the ability of the at least one non-active ingredient to react with all at least one sources of nicotine during storage is reduced or eliminated.

2. The pharmaceutical composition of claim 1, wherein the at least one source of nicotine is nicotine in the form of a free base, a salt, a complex, or a solvate.

3. The pharmaceutical composition of claim 1, wherein the at least one source of nicotine is nicotine polacrilex.

4. The pharmaceutical composition of claim 1, wherein the at least one source of nicotine is nicotine in a free base form.

5. The pharmaceutical composition of claim 1, wherein the at least one source of nicotine is nicotine tartrate or nicotine bitartrate.

6. The pharmaceutical composition of claim 1, wherein the at least one source of nicotine is a nicotine free base, and the nicotine free base is sorbed onto a second porous particulate carrier.

7. The pharmaceutical composition of claim 1, wherein the composition is in a form adapted for oral ingestion.

8. The pharmaceutical composition of claim 7, wherein the composition is in a form selected from the group consisting of gum, lozenge, tablet, and pouch product.

9. The pharmaceutical composition of claim 1, wherein the mixture comprises at least about 70 weight percent of the porous particulate carrier and up to about 30 weight percent of the at least one non-active ingredient, based on the total weight of the mixture.

10. The pharmaceutical composition of claim 1, wherein the mixture of porous particulate carrier and the at least one non-active ingredient further comprises an outer coating.

11. The pharmaceutical composition of claim 1, wherein the at least one source of nicotine is selected from the group consisting of nicotine in free base form, a nicotine salt, a resin complex of nicotine, and mixtures thereof; and the composition is in a pharmaceutically acceptable form adapted for oral ingestion of the composition.

12. A method for treating a human subject having a condition, disease, or disorder responsive to stimulation of nicotinic acetylcholinergic receptors, comprising orally or nasally administering an effective amount of a pharmaceutical composition according to claim 1 to said human subject.

13. The method of claim 12, wherein said administering step comprises administering the pharmaceutical composition to a human subject as a smoking cessation aid.

14. The method of claim 12, wherein the at least one source of nicotine is nicotine in the form of a free base, a salt, a complex, or a solvate.

15. The method of claim 12, wherein the at least one source of nicotine is nicotine polacrilex.

16. The method of claim 12, wherein the at least one source of nicotine is nicotine in a free base form.

17. The method of claim 12, wherein the at least one source of nicotine is nicotine tartrate or nicotine bitartrate.

18. The method of claim 12, wherein the at least one source of nicotine is nicotine free base, and the nicotine free base is sorbed onto a second porous particulate carrier.

* * * * *